United States Patent
Hansen et al.

(10) Patent No.: US 7,540,961 B2
(45) Date of Patent: Jun. 2, 2009

(54) METHODS FOR MANUFACTURING HYDROGEN USING ANAEROBIC DIGESTION

(75) Inventors: Conly L. Hansen, North Logan, UT (US); Dae-Yeol Cheong, Logan, UT (US)

(73) Assignee: Utah State University, North Logan, UT (US)

( * ) Notice: Subject to any disclaimer, the term of this patent is extended or adjusted under 35 U.S.C. 154(b) by 256 days.

(21) Appl. No.: 11/426,120

(22) Filed: Jun. 23, 2006

(65) Prior Publication Data

US 2006/0289355 A1      Dec. 28, 2006

Related U.S. Application Data

(60) Provisional application No. 60/693,710, filed on Jun. 24, 2005.

(51) Int. Cl.
*C02F 3/28* (2006.01)
*C02F 11/04* (2006.01)

(52) U.S. Cl. .................. 210/603; 210/613; 210/631

(58) Field of Classification Search .............. 210/603, 210/605, 612, 630, 631, 613
See application file for complete search history.

(56) References Cited

U.S. PATENT DOCUMENTS

| | | | | |
|---|---|---|---|---|
| 4,354,936 A | * | 10/1982 | Ishida et al. | 210/602 |
| 4,696,746 A | * | 9/1987 | Ghosh et al. | 210/603 |
| 4,696,747 A | * | 9/1987 | Verstraete et al. | 210/605 |
| 4,919,813 A | * | 4/1990 | Weaver | 210/603 |
| 5,464,539 A | * | 11/1995 | Ueno et al. | 210/603 |
| 6,416,993 B1 | * | 7/2002 | Wexler et al. | 435/262.5 |
| 6,860,996 B2 | | 3/2005 | Noike et al. | 210/603 |
| 2005/0064567 A1 | * | 3/2005 | Lay et al. | 435/168 |

OTHER PUBLICATIONS

M. Okamoto, T. Miyahara, O. Mizuno and T. Noike; Biological hydrogen potential of materials characteristic of the organic fraction of municipal solid wastes; Water Science and Technology, vol. 41 No. 3 pp. 25-32 IWA Publishing 2000.

Jiunn-Jyi Lay; Modeling and Optimization of Anaerobic Digested Sludge converting Starch to Hydrogen; Biotechnology and Bioengineering, vol. 68, No. 3, pp. 269-278 May 5, 2000.

Peter Setlow; Resistance of Bacterial Spores; Bacterial Stress Responses, Department of Biochemistry, University of Connecticut Health Center, Farmington, CT 06032, Chapter 14, pp. 217-230 2000 ASM Press, Washington D.C.

* cited by examiner

*Primary Examiner*—Fred Prince

(57) ABSTRACT

A method for manufacturing a biomass enriched with hydrogen-producing bacteria or spores includes providing a biomass comprising a hydrogen-producing bacteria and a competing bacteria and treating the biomass with a sufficient amount of a chemical agent for a period of time such that the treatment (i) kills, inhibits or injures substantially all of the competing bacteria and (ii) does not kill or inhibit the hydrogen-producing bacteria or causes the hydrogen-producing bacteria to form spores that are not destroyed during the chemical treatment. The method also includes digesting an enriched biomass with a non-sterile organic substrate. The enriched biomass includes hydrogen-producing bacteria or spores that are mixed in sufficient quantities with the organic substrate such that the hydrogen-producing bacteria can overcome the competing bacteria to consume the organic substrate and produce hydrogen.

35 Claims, No Drawings

METHODS FOR MANUFACTURING HYDROGEN USING ANAEROBIC DIGESTION

CROSS-REFERENCE TO RELATED APPLICATIONS

This Application claims the benefit of U.S. Provisional Patent Application No. 60/693,710, which was filed on Jun. 24, 2005, and which is hereby incorporated by reference in its entirety.

GOVERNMENT INTERESTS

Work described herein has been supported, in part by a grant from the United States Department of Agriculture, grant number NRCS 68-3A75-3-153. Therefore, the Government may have certain rights in this invention.

BACKGROUND OF THE INVENTION

1. The Field of the Invention

The present invention relates to the production of hydrogen from anaerobic digestion. In particular, the present invention relates to methods for enriching biomass with hydrogen-producing bacteria or spores and methods of producing hydrogen using the enriched biomass.

2. The Related Technology

Hydrogen is a potentially good fuel source for power generation and is currently used in many important industrial applications such as the manufacture of fertilizers. Although hydrogen is typically not used as a fuel source, hydrogen is often thought of as an environmentally superior fuel to hydrocarbons because when hydrogen is burned, it reacts with oxygen to produce environmentally harmless water. Unfortunately, hydrogen does not exist in nature in useable quantities; consequently, it has to be manufactured. Most hydrogen produced today is manufactured from hydrocarbons such as petroleum or natural gas. The disadvantage of manufacturing hydrogen from these is that they are expensive and non-renewable energy sources. Furthermore, hydrogen manufacturing using petroleum or natural gas consumes substantial amounts of energy and/or requires expensive catalysts, such as platinum based catalysts.

Anaerobic digestion provides a potentially improved alternative to manufacturing hydrogen from petroleum and natural gas. Anaerobic digesters can produce hydrogen from inexpensive and renewable energy sources such as organic wastes (e.g. food processing waste and animal waste). Recent studies have shown that certain strains of bacteria (e.g. bacteria from the genus *Clostridium*) are particularly effective at producing hydrogen as a by-product during anaerobic digestion of organic waste material.

One problem with digesting organic waste in an anaerobic digester is that organic waste such as manure includes naturally occurring bacteria. Many of these bacteria consume hydrogen. Eventually, an anaerobic digester fed with non-sterile material will create a bacterial culture that is a mixture of competing bacteria, some of which consume hydrogen. Absent some intervention, hydrogen-consuming bacteria will invariably grow until most or all of the hydrogen being produced is simultaneously consumed.

Several systems have been developed to allow hydrogen to be produced in an anaerobic digester. These systems typically require growing and maintaining pure strains of hydrogen-producing bacteria and sterilizing the material to be digested. These systems are not commercially viable because maintaining a pure strain of bacteria in a digester is difficult and sterilizing the material to be digested is very expensive.

Recently, an improved method has been developed for obtaining quantities of hydrogen-producing bacteria. In this method, a mixed culture of bacteria is heat treated to destroy the hydrogen-consuming bacteria. The hydrogen-producing bacteria survive the heat treatment by creating spores. Thus the treated culture is enriched with hydrogen-producing bacteria as compared to hydrogen-consuming bacteria. The enriched culture is then used to seed an anaerobic digester.

One problem with forming a seed culture using existing methods is that it requires an expensive heat treatment step. U.S. Pat. No. 6,860,996 to Noike et al, teaches reducing the cost of forming a seed culture by heat treating at temperatures between 68° C. and 95° C. While the Noike process may reduce costs, heat treating to above 68° C. is still expensive. Furthermore, Noike teaches sterilizing the material to be digested, which is also expensive.

Therefore, what is needed is a system for anaerobically digesting organic materials that is more cost effective and more efficient than existing systems.

BRIEF SUMMARY OF THE INVENTION

The present invention is directed to methods for generating hydrogen using anaerobic digestion. In one aspect of the invention a biomass is enriched with hydrogen-producing bacteria or spores by treating the biomass with a chemical agent. In another aspect of the invention, an enriched biomass is used in a bioreactor to aerobically digest a non-sterile organic substrate to produce hydrogen.

In an exemplary embodiment, the enriched biomass of the present invention is manufactured by treating a mixed culture of anaerobic bacteria with a chemical agent. The mixed culture is a biomass that includes at least one type of hydrogen-producing bacteria and at least one type of competing bacteria. The biomass is treated with a sufficient amount of the chemical agent for a period of time such that the treatment (i) kills substantially all of the competing bacteria and (ii) does not kill the hydrogen-producing bacteria and/or causes the hydrogen-producing bacteria to form spores that are not destroyed during the chemical treatment.

The chemical treatment of the present invention includes one or more of pH treatment, antibiotic treatment, methanogenic inhibitor treatment, similar chemical treatments, and combinations of the foregoing. In a preferred embodiment, the chemical treatment includes adjusting the pH to less than 3.5 alone or in combination with other bacteria killing treatments, including other chemical treatments. The inventors have found that adjusting the pH to less than 3.5 can have beneficial effects even where other treatments are used.

In a preferred embodiment, the chemical treatment of the biomass is carried out at a temperatures less than about 60° C., more preferably less than about 40° C., and most preferably at about ambient temperatures. Surprisingly, destroying or inhibiting hydrogen-consuming bacteria using a chemical treatment is still very effective at temperatures less than 60° C. While the present invention is not limited to chemical treatment at temperatures less than 60° C., substantial energy costs can be saved by performing the chemical treatment at temperatures less than 60° C.

Another aspect of the present invention includes digesting a non-sterile organic substrate (e.g. animal manure) using an enriched biomass. Because the organic substrate is non-sterile, it has competing bacteria such as methanogens or other hydrogenotrophic bacteria that can compete with hydrogen-producing bacteria for resources. The enriched biomass is mixed with the organic substrate in sufficient quantities that the hydrogen-producing bacteria in the enriched biomass overcome the competing bacteria in the organic substrate so as to digest the organic substrate and produce hydrogen.

In a preferred method of manufacturing hydrogen, the enriched biomass is manufactured according to the biomass enriching methods of the present invention. However, biomass enriched using other methods can be used in the present invention to digest a non-sterile organic substrate. For example, the enriched biomass can be manufactured by boiling or heat treating to a temperature between about 60° C. and boiling.

In a preferred embodiment the anaerobic digestion of the non-sterile substrate is performed in a semi-continuous sequencing batch digester. Preferably the pH in the sequencing batch digester is maintained between about 4.5 and 6.5 with a hydraulic retention time of between about 4 hours and about 16 hours. These pH ranges and hydraulic retention times have been found to improve hydrogen production rates in sequencing batch digesters.

These and other advantages and features of the present invention will become more fully apparent from the following description and appended claims as set forth hereinafter.

DETAILED DESCRIPTION OF EXEMPLARY EMBODIMENTS

I. Introduction and Definitions

In one aspect, the present invention includes manufacturing an enriched biomass using a chemical agent. Enriching the biomass using a chemical agent increases the concentration or activity of hydrogen-producing bacteria or spores in the biomass as compared to the concentration or activity of competing bacteria in the biomass. The biomass enriched according to the present invention can be advantageously used in a bioreactor to produce hydrogen.

Another aspect of the present invention is directed to a method of manufacturing hydrogen from a non-sterile substrate. The non-sterile substrate is digested by hydrogen-producing bacteria provided in an enriched biomass. The enriched biomass is combined with the non-sterile substrate in sufficient quantities such that the hydrogen-producing bacteria overcome competing bacteria to digest the organic substrate and produce hydrogen.

For purposes of the present invention, the term "non-sterile" refers to an organic material (e.g. biomass or substrate) that has been exposed to an environment for a sufficient time to ensure contamination of the organic material with one or more competing bacteria such as non-hydrogen-producing bacteria and/or hydrogen-consuming bacteria. Non-limiting examples of non-sterile materials include food processing waste and cow manure from a barnyard.

For purposes of the present invention, the term "contaminate" includes materials that have been intentionally inoculated with one or more types of bacteria.

For purposes of the present invention the term "enriched" as used with the term "biomass" does not necessarily require an increase in the number of hydrogen-producing bacteria or spores, although such may be the case. The term "enrich" refers mainly to the proportion of desired bacteria relative to undesired bacteria.

II. Methods of Manufacturing an Enriched Biomass

A. Components for Enriching a Biomass

The enriched biomass manufactured according to the present invention generally includes providing a mixture of anaerobic bacteria and treating the anaerobes with a suitable chemical agent to destroy or inhibit competing bacteria, such as hydrogen-consuming bacteria.

1. Mixtures of Anaerobes

The biomass is formed from a mixed culture of anaerobic bacteria. The mixed culture includes at least one type of hydrogen-producing bacteria and at least one type of competing bacteria. Mixed cultures of hydrogen-producing bacteria and competing bacteria are naturally occurring. Typically any anaerobic system operating under non-sterile conditions has hydrogen-producing bacteria and competing bacteria, absent some intervention. Suitable sources of biomass include traditional anaerobic digesters, lagoons, and other systems that have naturally occurring organic waste that is deprived of oxygen.

Any number and/or ratio of competing and hydrogen-producing bacterial species can be present in the biomass. Some common species of hydrogen-producing bacteria are members of the genus *Clostridium*. Members of the genus *Clostridium* are gram-positive, spore forming rods that are anaerobic. Hydrogen-producing bacteria from the genus *Clostridium* include *C. buyricum, C. acetobutryicum, C. butylicum, C. kluyveri,* and *C. Pasteurianum*. Other examples of a hydrogen-producing bacterium include *Enterobacteriacea, Lactobacillus, Bacillaceae.*

Examples of hydrogen-consuming bacteria include most methanogens including *Methanosarcina* and *Methanothrix*.

While particular species of bacteria can be selected for use in the biomass, in a preferred embodiment, the hydrogen-producing bacteria and the competing bacteria are simply selected by virtue of their existing naturally in a non-sterile anaerobic material. Using a non-sterile anaerobic material is advantageous over sterile anaerobic material because it is expensive to produce and maintain sterile conditions. Even where sterile conditions can be feasibly maintained, it can still be advantageous to begin with a naturally existing biomass. This is because if the hydrogen-producing bacteria are selected from nature, regulations controlling the release of these bacterial species back into the environment are more lenient.

2. Chemical Agent

The chemical agent is selected to cause a bacterial stress response and/or an inhibitory effect on bacteria in the biomass. The chemical agent can increase the number or activity of hydrogen-producing bacteria or spores. Alternatively the chemical agent can decrease the concentration or activity of competing bacteria or spores. Suitable chemical agents include acids, antibiotics, methanogen inhibitors, and the like.

Suitable acids include perchloric acid, sulfuric acid, phosphoric acid, hydrochloric acid, nitric acid, and combinations thereof. Other acids such as organic acids can also be used. Typically the acid is selected according to cost. However, other factors such as safety, dilution of the biomass, and the introduction of particular ions into the system can also influence the selection of the acid.

Chemical agents can be selected to destroy or inhibit particular bacteria. For example, methanogen inhibitors are selected to inhibit the growth of methanogens, which are known to consume hydrogen. An example of a suitable methanogen inhibitor is sodium 2-bromoethanesulfonate. Antibiotics can also be used to inhibit growth of hydrogen-consuming bacteria. An example of a suitable antibiotic is rumensin.

B. Treating the Biomass to Form an Enriched Biomass

The biomass is treated with one or more chemical agents to induce one or more of a bacterial stress response in the hydrogen-producing bacteria, to destroy the hydrogen-consuming bacteria, or to inhibit growth of the hydrogen-consuming bacteria. In each case, the result is that the growth, concentration, and/or activity of the hydrogen-producing bacteria is increased over the growth, concentration, and/or activity of the hydrogen-consuming bacteria as compared to the untreated biomass. Thus, the chemical treatment of the present invention produces an enriched biomass.

As mentioned above, chemical treatments include acid treatment, methanogenic inhibitor treatment, antibiotic treatment, and the like. These treatments can be performed individually or in combination with additional treatments. Treatments that can be performed in addition to chemical treatment include heat treating, dessication, and freeze-thaw. Other treatments known to induce bacterial stress responses can also be used with the chemical treatment of the present invention.

Any number of chemical treatments can be performed on the biomass for any duration of time so long as the treatment does not completely destroy the hydrogen-producing bacteria or spores. In other words, the chemical treatment, in combination with any additional treatments, should be harsh enough to inhibit or destroy hydrogen-consuming bacteria but leave sufficient hydrogen-producing bacteria or spores to create the enriched biomass. Typically a sliding scale exists between the harshness of a treatment and the duration of a treatment; the harsher the conditions imposed on the biomass (e.g. the lower the pH), the less time that is needed to perform the treatment.

In an exemplary embodiment, the chemical treatment is performed using an acid. The acid is added to the biomass to adjust the pH to between about 1.5 and about 3.5, more preferably between about 1.5 and about 2.7, and most preferably between about 1.7 and about 2.3. The duration and temperature of the acid treatment are preferably in a range of about 5 to about 20 minutes at about 4° C. to about 20° C. The duration and temperature needed typically depends on the volume of biomass being used.

The inventors of the present invention have found that the enriched biomass of the present invention can be formed without heat treating by lowering the pH of the biomass substantially below 3.7. Because the pH scale is a logarithmic scale, small adjustments in pH can have a significant effect on acid concentration. By increasing the acid concentration by 58%, or more preferably by 100% (i.e. from pH 3.7 to pH 3.5 or more preferably to pH 3.4), hydrogen-consuming bacteria can be inhibited or destroyed, or both, while eliminating or substantially reducing need to heat the system. At a pH of about 3.5, the acid concentration begins to be sufficient such that elevated temperatures are not needed for destroying or inhibiting bacteria in the biomass. In this embodiment, controlling temperature can still be important, but the temperature is controlled to influence the growth of bacteria or to influence the effectiveness of the chemical agents, or both.

In an exemplary embodiment, the chemical treatment can be performed in one or more stages. For example, acidification can be performed at more than one pH. In an exemplary embodiment, the biomass is acidified to a pH between about 3.0 and about 3.5 and held at the adjusted pH for between about 2 hours and about 10 days. In a second stage, the pH of the biomass is adjusted to between about 1.5 and 2.7 and held at the adjusted pH for about 10 min to about 2 days.

In an exemplary embodiment, a combination of treatments is performed. In a preferred embodiment, the combination of treatments includes at least adjusting the pH to between about 2.5 to about 3.5. Suitable treatments that can be performed in combination with an acid treatment between about 2.5 and about 3.5 include the addition of a methanogen inhibitor, desiccation, freeze thaw, and use of an antibiotic. The combination of treatments can be performed simultaneously or sequentially.

The use of a combination of treatments can be particularly beneficial for the process of manufacturing enriched biomass. Using a combination of treatments allows the harshness of individual treatments to be reduced. Reducing the harshness of the individual treatments is advantageous because harsh conditions can adversely affect hydrogen-producing bacteria or spores.

In one embodiment, the chemical agent and its concentration is selected to induce a bacterial stress response in the hydrogen-producing bacteria. The inventors currently believe that many of the hydrogen-producing bacteria in naturally occurring biomass such as cow manure are spore formers. The harsh environment created by the presence of the chemical agent induces a bacterial stress response that causes the hydrogen-producing bacteria to form spores. In this embodiment, the chemical agent destroys substantially all of the growing hydrogen-consuming bacteria and may even destroy some or all of the growing hydrogen-producing bacteria. However, because the hydrogen-producing bacteria advantageously form spores, the biomass is enriched with hydrogen-producing bacteria or spores.

Performing a combination of treatments simultaneously (instead of sequentially) can advantageously promote a bacterial stress response. For example, in a preferred embodiment, acid treating to a pH between about 2.5 and about 3.5 is simultaneously performed in combination with a methanogen inhibitor treatment to induce a bacterial stress response. The bacterial stress response using the combination of treatments is greater than the bacterial stress response of the two treatments performed sequentially. However, the induced bacterial stress response according to the present invention is not limited to performing a combination of treatments or to combinations of treatments performed simultaneously.

III. Methods for Manufacturing Hydrogen from a Non-Sterile Substrate Using an Enriched Biomass The present invention is directed to methods for manufacturing hydrogen from a non-sterile substrate using an enriched biomass. The methods of manufacturing hydrogen according to the present invention generally include (i) providing an enriched biomass (ii) providing an organic substrate that includes at least one type of competing bacteria, and (iii) digesting a mixture of enriched biomass and organic substrate such that the hydrogen-producing bacteria substantially overcome the competing bacteria.

A. Providing an Enriched Biomass

Any biomass enriched with hydrogen-producing bacteria can be used with the systems of the present invention for producing hydrogen. As discussed above, an enriched biomass is an organic material that has been treated to have predominately hydrogen-producing bacteria or spores after germination. The enriched biomass can include hydrogen-producing bacteria or spores that when germinated form hydrogen-producing bacteria. In a preferred embodiment, the enriched biomass is manufactured by treating the biomass with a chemical agent as described above.

The enriched biomass used in the digestion system of the present invention can be manufactured in any way so long as the enriched biomass can seed the digester system with sufficient hydrogen-producing bacteria. While enriched biomass manufactured using a chemical agent is presently preferred, enriched bacteria manufactured using other methods can be used. Examples of other enriched biomass types include biomass that is enriched through a heat treatment at temperatures between 68° C. and 95° C. or by boiling. An example of an enriched biomass manufactured using heat treatment is disclosed in U.S. Pat. No. 6,860,996 to Noike et al., which is incorporated herein by reference.

In yet another embodiment, the enriched biomass is manufactured using a pure strain of a hydrogen-producing bacteria. Those skilled in the art are familiar with methods for culturing a biomass to contain pure strains of hydrogen-producing bacteria.

B. Providing an Organic Substrate

Any organic substrate that has at least one type of competing bacteria can be used with the methods of the present invention. Competing bacteria are bacteria that are non-hydrogen-producing or hydrogen-consuming bacteria. These bacteria compete with the hydrogen-producing bacteria for resources (e.g. organic substrate) in the system. Examples of competing bacteria include methanogens and sulfate-reducing bacteria.

The organic substrate is typically a low value or negative value energy source. Examples of suitable organic substrates include food processing waste such as starches from potato processing, cheese whey, or deproteinated cheese whey, which are waste product from cheese production. Another source of organic substrate is animal wastes such as cow and pig manure and human waste.

As mentioned, the organic substrate includes at least one type of competing bacteria. The competing bacteria are typically present in the organic substrate as a consequence of handling the organic substrate and are often provided for by the natural environment. For example animal wastes are almost always contaminated with many different kinds of bacteria as they are disposed of. Food processing waste can be contaminated by exposure to the environment or by inoculation. For example, cheese whey contains competing bacteria that are used in the cheese manufacturing process.

C. Digestion Systems

Digester systems suitable for use with the present invention include continuous-flow stirred tank reactors, and anaerobic sequencing batch reactors, upflow anaerobic digesters, and induced blanket reactors. Those skilled in the art of anaerobic digestion are familiar with these and similar bioreactors that are suitable for fermenting organic materials using anaerobes. In a preferred embodiment, a sequencing batch reactor is employed because of its ability to maintain high levels of biomass as compared with continuous flow stirred tank reactors. Even more preferred is a semi-continuous fed-sequencing batch digester, which is similar to a sequencing batch digester but continuously or semi-continuously feeds substrate into the reactor.

D. Seeding The Digester To Produce Hydrogen

The methods of the present invention include seeding the organic substrate with the enriched biomass and digesting the mixture in an anaerobic digester to produce hydrogen. The enriched biomass is added to the digester in sufficient quantities such that the hydrogen-producing bacteria can substantially overcome the competing bacteria in the organic substrate so as to allow the hydrogen-producing bacteria to digest the organic substrate thereby producing hydrogen. In a preferred embodiment, the hydrogen-producing bacteria at least overcome the hydrogen-consuming bacteria as these bacteria can be more detrimental to the collection of hydrogen gas than other competing bacteria. For example, in a preferred embodiment, the concentration or activity of methanogenic bacteria is controlled by adding hydrogen-producing bacteria in sufficient quantities to the bioreactor.

The amount of enriched biomass that is needed to substantially overcome the competing bacteria depends on the concentration and activity of the hydrogen-producing bacteria or spores in the enriched biomass and the concentration and activity of the competing bacteria in the organic substrate.

In an exemplary embodiment, the sufficiency of the ratio of enriched biomass to substrate is determined by monitoring the ratio of gasses being evolved from the digester. For example, significant amounts of methane in the gas effluent indicate that methanogenic bacteria in the culture are competing strongly for substrate. In another exemplary method, the ratio of hydrogen to carbon dioxide can be monitored. Typically a decrease in the ratio of hydrogen to carbon dioxide indicates that non-hydrogen-producing bacteria are competing for substrate.

In yet another embodiment, the sufficiency of the ratio of enriched biomass to substrate is determined by monitoring components of the supernatant of the effluent. For example, hydrogen-producing bacteria are known to produce volatile fatty acids. Thus, volatile fatty acids, such as acetate, butyrate, caproate, and valerate, can be monitored to determine the effectiveness of the hydrogen-producing bacteria. In one embodiment, the butyrate to acetate ratio in the volatile fatty acids can be monitored as an indicator for activity of hydrogen-producing bacteria. Higher ratios of butyrate to acetate indicate high activity of hydrogen-producing bacteria. If needed, the ratio of enriched biomass to substrate is regulated to compete with the non-hydrogen-producing bacteria or hydrogen-consuming bacteria.

Surprisingly, small ratios of enriched biomass to organic substrate can be sufficient for overcoming the competing bacteria. Depending on the concentration of competing bacteria an enriched biomass manufactured using a chemical treatment according to the present invention can be combined with organic substrate in a ratio greater than about 1:20, more preferably in a ratio greater than about 1:10, and most preferably greater than about 1:5.

Including a sufficient amount of biomass to allow the hydrogen-producing bacteria to overcome the competing bacteria does not mean that the competing bacteria are eliminated from the system. As those skilled in the art will appreciate, bacterial systems can have two or more bacteria where one species dominates over the other species but does not eliminate the minority species. Often this dominance can be maintained simply by virtue of having an initially dominating concentration.

How the digester is loaded can also have an effect on how well the hydrogen-consuming bacteria overcome the competing bacteria. Two methods that are particularly effective for allowing the hydrogen-producing bacteria to overcome the competing bacteria include a spread loading technique and a continuous feed technique.

1. Spread Loading Technique

In an exemplary embodiment the enriched biomass is combined with the organic substrate by spreading the loading of the organic substrate over time. In this embodiment, a digester is seeded with the enriched biomass and the organic substrate is fed over a period of time. By delaying the feed time, the hydrogen-producing bacteria are better able to overcome the competing bacteria, thereby reducing the amount of enriched biomass that needs to be added.

In a preferred embodiment the spread loading is performed over a time period of about ½ to ¾ the full retention time, which includes loading, mixing, settling and decanting in an anaerobic sequencing batch reactor. However, the loading can be spread over essentially the entire retention time, which is typically the case for upflow anaerobic digesters. In one embodiment, loading is performed during nearly the entire mixing phase. For substrate that is more difficult to break down, it can be advantageous to continue mixing for several hours following spread loading.

2. Continuous Feed or Semi-Continuous Feed Technique

In an alternative embodiment, the digester is loaded using a continuous or semi-continuous feeding technique. In this embodiment, a mixture of an organic substrate and the enriched biomass is continuously or semi-continuously fed into the digester. By continuously or semi-continuously feeding enriched biomass with the organic substrate, the digester is continually stocked with hydrogen-producing bacteria to ensure that the hydrogen-producing bacteria can overcome the competing bacteria in the substrate.

In this embodiment, the enriched biomass can be mixed with the organic substrate prior to placement into the digester or they can be added separately. In addition, the enriched biomass and the organic substrate can be added to the digester simultaneously or in an alternating sequential manner.

The continuous feed technique can be used with any digester where substrate is being continuously or semi-continuously fed to the digester. The continuous feed technique is particularly suited for a semi-continuous anaerobic sequencing batch digester, although the technique can be used with other digester systems and sequencing batch digesters can be used without the continuous or semi-continuous technique.

E. Operating the Digester

The digesters of the present invention, like most digesters, can operate under varying conditions. However, digester conditions are preferably optimized to maximize hydrogen production or substrate digestion or both. One parameter that can substantially influence hydrogen production is pH. In a preferred embodiment, pH is maintained between about 4.5 and about 9.0, more preferably between about 5.0 and about 8.0 and most preferably between about 5.0 and about 6.5.

Hydraulic retention time can also be controlled to optimize hydrogen production in a continuous or semi-continuous fed digester. Hydraulic retention time is preferably maintained between about 4 hours and about 16 hours, more preferably between about 6 hours and 12 hours, and most preferably between about 7 and about 9 hours.

F. Pre-Culture of Enriched Biomass

As discussed above, the enriched biomass of the present invention can include hydrogen-producing bacteria in the form of spores. In a preferred embodiment, an enriched biomass that includes spores is cultured before it is digested with the organic substrate thereby germinating the spores. Culturing the enriched biomass prior to digestion was found to have a significant effect on hydrogen production. It is believed that culturing the enriched bacteria prior to digestion allows the spores to germinate such that when the organic substrate is inoculated, the hydrogen-producing bacteria are actively dividing such that they can more easily overcome the competing bacteria. In a preferred embodiment, the spores are germinated and the bacteria growing therefrom are cultured for a sufficient time and at a sufficient temperature such that the bacteria are in exponential growth.

In an exemplary embodiment, the enriched biomass is precultured by culturing the biomass with a sugar based substrate between about 25° C. and about 40° C. for between about 10 hours and about 80 hours. Typically culture times vary with temperature.

The following examples provide exemplary conditions for carrying out the present invention according to one embodiment of the invention.

EXAMPLE 1

Manufacture of Enriched Biomass

Sludge was obtained from the bottom portion of an induced blanket reactor at a cattle manure wastewater treatment plant. Raw sludge was filtered through a screen (pore size: 2 mm) to remove fiber-like undigested material. The filtered raw sludge was suspended at pH 3. The pH of the sludge was adjusted using 10N hydrochloric acid. The sludge was then acclimated at 35.5±0.5° C. and held for between about 24 and about 72 hours. The acid treated sludge possessed characteristics of dominant *Clostridia* (i.e. a biomass enriched with *Clostridia*, which is a hydrogen-producing bacteria).

EXAMPLES 2-6

Induced Bacterial Stress Response

In Examples 2-7, an additional treatment was performed on the acid treated sludge of Example 1 to cause a bacterial stress response in the *Clostridia* bacteria. The bacterial stress response caused the *Clostridial* species to form spores. In Example 2, the acid treated sludge of Example 1 was boiled for 20 min. at 95° C. (84.55 kPa pressure). In Example 3, the acid treated sludge of Example 1 was treated with 1M sodium 2-bromoethanesulfonate ($C_2H_4BrO_3SNa$), which is a methanogen inhibitor. In Example 4, the acid treated sludge of Example 1 was treated with 0.5M sodium 2-bromoethanesulfonate. In Example 5, the acid treated sludge of Example 1 was treated with perchloric acid ($HClO_4$) to adjust the pH to 2.0. In Example 6 the acid treated sludge of Example 1 was frozen at −10° C. for 24 hours and then thawed for 12 hours in a water bath at 25° C. In Example 7, the acid treated sludge of Example 1 was dried and desiccated at 105° C. for 4 hours.

The treatments in Examples 2-7 caused the *Clostridial* species to form spores thereby enriching the biomass (i.e. the sludge). The biomasses were enriched by either a reduction of competing bacteria or by an increase in the number of hydrogen-producing bacteria or spores.

Experiments were carried out in duplicate or triplicate to assess the enhanced hydrogen production optional of the enriched biomasses manufactured in Examples 2-7. These enriched biomasses were added at equal volumes to serum bottles with a working volume of 130 ml at an initial pH 7 at 35.5±0.5° C. for about 168 hours. A carbohydrate based substrate with a COD value of 25,000 mg $l^{-1}$ was fed to the enriched biomass. The results are shown below in Table 1, which gives the ml of hydrogen produced. Table 1 shows two rows of data labeled "Run 1" and "Run 2", which are data sets generated from the duplicate biomasses that were manufactured, as mentioned above.

TABLE 1

| Batches | Example 2 Boiling | Example 3 Methanogen Inhibitor 1.0 M | Example 4 Methanogen Inhibitor 0.5 M | Example 5 Acid Treating to pH 2.0 | Example 6 Freeze Thaw | Example 7 Desiccation | Control |
|---|---|---|---|---|---|---|---|
| Run 1 | 117.4 ± 20.0 | 237.8 ± 3.1 | 227.6 ± 0.9 | 221.6 ± 0.1 | 135.8 ± 30.5 | 203.5 ± 18.8 | 15.0 ± 4.0 |
| Run 2 | 147.9 ± 8.7 | 185.1 ± 63.8 | 277.5 ± 3.5 | 418.9 ± 28.0 | 300.5 ± 13.8 | 315.9 ± 3.3 | 50.3 ± 1.3 |
| Average | 132.7 (4.07) | 211.4 (6.49) | 252.5 (7.75) | 320.2 (9.82) | 218.2 (6.69) | 259.7 (7.97) | 32.6 (—) |

As can be seen from the results, perchloric acid treatment to pH 2.0 showed the greatest improvement in hydrogen production. However, all the methods showed a significant improvement over no additional treatment.

EXAMPLES 8-13

The data given in Table 2, below, was from experiments prepared according to the experiments for Table 1, except that no preacidification was applied. The results of the digestion are labeled as "Run 3", which gives the total amount of hydrogen gas produced during digestion.

TABLE 2

| | Example 8 Boiling | Example 9 Methanogen Inhibitor 1.0 M | Example 10 Methanogen Inhibitor 0.5 M | Example 11 Acid Treating to pH 2.0 | Example 12 Freeze Thaw | Example 13 Desiccation | Control |
|---|---|---|---|---|---|---|---|
| Run 3 | 186.5 ± 47 (3.08) | 175.8 ± 20.3 (2.91) | 264.5 ± 17.7 (4.37) | 311.0 ± 13.2 (5.14) | 126.9 ± 6.3 (2.10) | 116.7 ± 9.2 (1.93) | 60.5 ± 3 (—) |

In examples 8-13, the acid treatment to pH 2.0 had the most beneficial effect on hydrogen production. However, all the treatments had a significant improvement over the control.

The following examples provide exemplary conditions for manufacturing hydrogen from a non-sterile organic substrate using an enriched biomass.

EXAMPLE 14

Hydrogen Manufactured From Non-Sterile Substrate

An enriched biomass manufactured according to Example 5 was digested with a non-sterile organic substrate in a semi-continuous anaerobic sequencing batch digester. The organic substrate consumed in the digester contained a total chemical oxygen demand of 25,000 mg $l^{-1}$, which was primarily from glucose. The competing bacteria were unknown microflora produced by virtue of non-sterile conditions. The ratio of enriched biomass to organic substrate was about 1:9. The enriched biomass was digested in two phases. During phases I the hydraulic retention time was varied between 8 and 16 hours and during Phase II the hydraulic retention time was varied between about 4 and 12 hours. Phases I and II were both conducted at steady state with the pH between about 5.2 and 6.2. Tables 3 below show the gas production during phase I.

TABLE 3

| Run | HRT (h) | pH | VOLR[a] (g COD $l^{-1}$ day$^{-1}$) | Feed | Reaction | Settle | Decant | Total | $H_2$[b] (ml $l^{-1}$ day$^{-1}$) |
|---|---|---|---|---|---|---|---|---|---|
| | | | | | (Cycle 1) | | | | |
| 1 | 16 | 5.2 | 37.5 | 20 | 430 | 30 | 20 | 480 | 1840 ± 160 |
| 2 | 16 | 6.2 | 37.5 | 20 | 430 | 30 | 20 | 480 | 2160 ± 40 |
| 3 | 12 | 5.7 | 50.0 | 20 | 310 | 30 | 20 | 360 | 2110 ± 30 |
| 4 | 8 | 5.2 | 75.0 | 20 | 190 | 30 | 20 | 240 | 2370 ± 310 |
| 5 | 8 | 6.2 | 75.0 | 20 | 190 | 30 | 20 | 240 | 3710 ± 460 |

TABLE 3-continued

| | | | VOLR[a] | Cycle time (min.) | | | | | $H_2$[b] |
|---|---|---|---|---|---|---|---|---|---|
| Run | HRT (h) | pH | (g COD $l^{-1}$ day$^{-1}$) | Feed | Reaction | Settle | Decant | Total | (ml $l^{-1}$ day$^{-1}$) |
| | | | | (Cycle 2) | | | | | |
| 6 | 16 | 5.2 | 37.5 | 20 | 430 | 30 | 20 | 480 | 1730 ± 120 |
| 7 | 16 | 6.2 | 37.5 | 20 | 430 | 30 | 20 | 480 | 1860 ± 40 |
| 8 | 12 | 5.7 | 50.0 | 20 | 310 | 30 | 20 | 360 | 2610 ± 10 |
| 9 | 8 | 5.2 | 75.0 | 20 | 190 | 30 | 20 | 240 | 2310 ± 30 |
| 10 | 8 | 6.2 | 75.0 | 20 | 190 | 30 | 20 | 240 | 2640 ± 540 |

[a]Volumetric organic loading rate
[b]Mean ± standard error (n = 3-6)

Table 4 below shows hydrogen production during phase II.

TABLE 4

| | | | VOLR[a] | Cycle time (min.) | | | | | $H_2$[b] |
|---|---|---|---|---|---|---|---|---|---|
| Run | HRT (h) | pH | (g COD $l^{-1}$ day$^{-1}$) | Feed | Reaction | Settle | Decant | Total | (ml $l^{-1}$ day$^{-1}$) |
| | | | | (Cycle 1) | | | | | |
| 11 | 12 | 5.2 | 50.0 | 20 | 310 | 30 | 20 | 360 | 2996 ± 283 |
| 12 | 12 | 6.2 | 50.0 | 20 | 310 | 30 | 20 | 360 | 3194 ± 208 |
| 13 | 8 | 5.7 | 75.0 | 20 | 190 | 30 | 20 | 240 | 4459 ± 652 |
| 14 | 4 | 5.2 | 150.0 | 20 | 70 | 30 | 20 | 120 | 2582 ± 283 |
| 15 | 4 | 6.2 | 150.0 | 20 | 70 | 30 | 20 | 120 | 2624 ± 92 |
| | | | | (Cycle 2) | | | | | |
| 16 | 12 | 5.2 | 50.0 | 20 | 310 | 30 | 20 | 360 | 3963 ± 167 |
| 17 | 12 | 6.2 | 50.0 | 20 | 310 | 30 | 20 | 360 | 5233 ± 40 |
| 18 | 8 | 5.7 | 75.0 | 20 | 190 | 30 | 20 | 240 | 5535 ± 553 |
| 19 | 4 | 5.2 | 150.0 | 20 | 70 | 30 | 20 | 120 | 1634 ± 109 |
| 20 | 4 | 6.2 | 150.0 | 20 | 70 | 30 | 20 | 120 | 2656 ± 186 |

[a]Volumetric organic loading rate
[b]Mean ± standard error (n = 3-6)

The total gas concentration was dependent on hydraulic retention time with a low production rate of 5200-6000 ml $l^{-1}$ day$^{-1}$ at the hydraulic retention time of 16 h and a high production rate of 11,000-14,000 ml $l^{-1}$ day$^{-1}$ at the hydraulic retention time of about 4 h. The hydrogen gas content in the total gas produced decreased to a low value of 13-25% at the hydraulic retention time of 4 h, compared to 30%-57% at the hydraulic retention time of 8, 12 and 16 h.

Thus the optimum conditions for hydrogen production were achieved at an observed design point of a hydraulic retention time of 8 h and a pH of 5.7. At this hydraulic retention time hydrogen production was 4460-5540 ml $l^{-1}$ day$^{-1}$ with a hydrogen composition of 43%-57% with no methane.

The biomass concentration increased from about 2.5 g to about 17.5 g (VSS $l^{-1}$) throughout the runs of the anaerobic sequencing batch reactor. These values were significantly higher than the about 0.9 g to about 1.5 g (VSS $l^{-1}$) observed for continuously stirred reactors. The increase in the level of biomass was determined to be the result of the physical configuration of the anaerobic sequencing batch digester and was not dependent on hydraulic retention time or pH.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of forming a biomass enriched with hydrogen-producing bacteria or spores, comprising:
    providing a biomass comprising at least one type of hydrogen-producing bacteria and at least one type of competing bacteria; and
    treating the biomass with a sufficient amount of at least one chemical agent for a period of time such that the treatment (i) kills, inhibits, or injures substantially all of the competing bacteria and (ii) does not kill or inhibit the at least one type of hydrogen-producing bacteria and/or causes the at least one type of hydrogen-producing bacteria to form spores that are not destroyed during the chemical treatment,
    wherein the chemical treatment is performed at one or more temperatures less than about 60° C.

2. A method as in claim 1, wherein the chemical agent is selected from the group consisting of an acid, a methanogenic inhibitor, an antibiotic, and combinations thereof.

3. A method as in claim 1, wherein the chemical treatment is performed at one or more temperatures less than about 40° C.

4. A method as in claim 1, wherein the chemical treatment is performed at substantially ambient temperatures.

5. A method as in claim 1, wherein the chemical treatment is carried out for more than about 1 hour.

6. A method as in claim 1, wherein the chemical agent is an acid that is added to lower the pH of the biomass to between about 1.5 and about 3.5.

7. A method of manufacturing hydrogen comprising:
placing an amount of the enriched biomass of claim 1 in an anaerobic digester;
placing an organic substrate in the anaerobic digester; and
holding the enriched biomass and the organic substrate at conditions suitable for anaerobic digestion such that hydrogen-producing bacteria grow from the enriched biomass and degrade the organic substrate to produce hydrogen.

8. A method as in claim 7, wherein the enriched biomass comprises spores and the method further comprises germinating the spores prior to placing the biomass into the anaerobic digester.

9. A method as in claim 7, wherein the ratio of enriched biomass to substrate is greater than 1:50.

10. A method for manufacturing hydrogen from a non-sterile organic material, comprising:
providing an enriched biomass comprising spores of one or more types of hydrogen-producing bacteria or spores, wherein the biomass is manufactured according to the method of claim 1;
providing an organic substrate contaminated with at least one or more types of competing bacteria, wherein the competing bacteria are hydrogen-consuming bacteria or bacteria that do not produce hydrogen;
culturing the enriched biomass to germinate the spores;
digesting the cultured, enriched biomass and the organic substrate in a digester under anaerobic conditions, wherein the enriched biomass is added to the digester in sufficient quantities such that the hydrogen-producing bacteria can substantially overcome the competing bacteria so as to allow the hydrogen-producing bacteria to digest the organic substrate to produce hydrogen; and
collecting the hydrogen gas produced therefrom.

11. A method as in claim 10, wherein the ratio of enriched biomass to organic substrate is greater than about 1:20.

12. A method as in claim 10, wherein the ratio of enriched biomass to organic substrate is greater than about 1:5.

13. A method as in claim 10, wherein the digesting is performed in a semi-continuous sequencing batch digester.

14. A method as in claim 10, wherein the digesting is performed in a continuous mix digester.

15. A method as in claim 10, further comprising loading the enriched biomass into the digester and spreading the loading of the organic substrate over a period of time greater than about ¼ of the total retention time so as to allow the hydrogen-producing bacteria to more easily overcome the competing bacteria.

16. A method as in claim 10, wherein the organic substrate and the enriched biomass are continuously or semi-continuously fed into the digester.

17. A method as in claim 10, wherein digestion is performed at a temperature between about 25° C. and about 45° C.

18. A method as in claim 10, wherein digestion is carried out for less than about 80 hours.

19. A method as in claim 10, wherein the hydraulic retention time is maintained between about 4 hours and about 16 hours.

20. A method as in claim 10, wherein the hydraulic retention time is maintained between about 6 hours and 12 hours.

21. A method as in claim 10, wherein the enriched biomass comprises spores and the system further comprises germinating the spores prior to digesting the organic substrate therewith.

22. A method as in claim 21, wherein the spores are germinated and the bacteria are cultured for a sufficient time and at a sufficient temperature such that the hydrogen-producing bacteria are in exponential growth.

23. A method for manufacturing an enriched biomass for use in anaerobic digestion, comprising:
providing a biomass comprising at least one type of a hydrogen-producing bacteria and at least one type of competing bacteria;
adjusting the pH of the biomass to a pH between about 1.5 and about 3.5; and
holding the biomass at the adjusted pH to induce a bacterial stress response that causes the hydrogen-producing bacteria to form spores.

24. A method as in claim 23, wherein the pH is at least partially adjusted using an acid selected from the group consisting of perchloric acid, sulfuric acid, phosphoric acid, hydrochloric acid, nitric acid, and combinations thereof.

25. A method as in claim 23, wherein inducing the bacterial stress response further comprises treating the biomass using one or more of an antibiotic, a methaneogenic inhibitor, desiccation, or a heat treatment.

26. A method as in claim 23, wherein the acid treatment is carried out at a temperature less than about 60° C.

27. A method for manufacturing hydrogen from a non-sterile organic material, comprising:
providing an enriched biomass comprising spores of one or more types of hydrogen-producing bacteria or spores, wherein the biomass is manufactured according to the method of claim 23;
providing an organic substrate contaminated with at least one or more types of competing bacteria, wherein the competing bacteria are hydrogen-consuming bacteria or bacteria that do not produce hydrogen;
culturing the enriched biomass to germinate the spores;
digesting the cultured, enriched biomass and the organic substrate in a digester under anaerobic conditions, wherein the enriched biomass is added to the digester in sufficient quantities such that the hydrogen-producing bacteria can substantially overcome the competing bacteria so as to allow the hydrogen-producing bacteria to digest the organic substrate to produce hydrogen; and
collecting the hydrogen gas produced therefrom.

28. A method as in claim 27, wherein the ratio of enriched biomass to organic substrate is greater than about 1:20.

29. A method as in claim 27, wherein the ratio of enriched biomass to organic substrate is greater than about 1:5.

30. A method as in claim 27, further comprising loading the enriched biomass into the digester and spreading the loading of the organic substrate over a period of time greater than about ¼ of the total retention time so as to allow the hydrogen-producing bacteria to more easily overcome the competing bacteria.

31. A method as in claim 27, wherein digestion is performed at a temperature between about 25° C. and about 45° C.

32. A method as in claim 27, wherein digestion is carried out for less than about 80 hours.

33. A method as in claim 27, wherein the hydraulic retention time is maintained between about 4 hours and about 16 hours.

34. A method as in claim 27, wherein the enriched biomass comprises spores and the system further comprises germinating the spores prior to digesting the organic substrate therewith.

35. A method as in claim 34, wherein the spores are germinated and the bacteria are cultured for a sufficient time and at a sufficient temperature such that the hydrogen-producing bacteria are in exponential growth.

* * * * *